United States Defensive Publication [19] (H) [11] T101,101

Kogon [43] Oct. 6, 1981

[54] PROCESS FOR PREPARING A SMALL PARTICLE SIZE DISPERSION OF A COMPLEX OF 4,4'-METHYLENEDIANILINE WITH A SALT

[76] Inventor: Irving C. Kogon, 1420 Drake Rd., Wilmington, Del. 19803

[21] Appl. No.: 220,853

[22] Filed: Dec. 29, 1980

Related U.S. Application Data

[63] Continuation of Ser. No. 97,233, Nov. 26, 1979.

[51] Int. Cl.[3] ..... C07C 87/50

[52] U.S. Cl. ..... 564/334; 564/330

[57] ABSTRACT

Preparing a dispersion of methylenedianiline/inorganic salt complex curing agent of small particle size which comprises: (a) agitating while reacting 3 moles of 4,4'-methylenedianiline with not less than 1 mole of a salt selected from the group consisting of sodium chloride, sodium bromide, sodium iodide, lithium chloride, lithium bromide and lithium iodide in the presence of water and a benzenoid hydrocarbon solvent for the methylenedianiline; (b) separating the resulting complex having an average particle size diameter of less than about 10 μm from the bulk of the hydrocarbon solvent; (c) drying said complex; and (d) dispersing said complex in a substantially nonvolatile liquid carrier that is inert to the complex; with the proviso that steps (c) and (d) can be carried out in any order or substantially simultaneously.

8 Claims, No Sheets Drawing,

13 Pages Specification

The file of this unexamined application may be inspected and copies thereof may be purchased (849 O.G. 1221, Apr. 9, 1968).